(12) United States Patent
Meitner

(10) Patent No.: US 7,845,943 B2
(45) Date of Patent: Dec. 7, 2010

(54) METHOD FOR MAKING AND USING A TEMPLATE FOR LOCATING A DENTAL IMPLANT AND COMPONENTS RELATING THERETO

(76) Inventor: Sean W. Meitner, 6248 S. Hill Rd., Middlesex, NY (US) 14507

(*) Notice: Subject to any disclaimer, the term of this patent is extended or adjusted under 35 U.S.C. 154(b) by 260 days.

(21) Appl. No.: 11/851,250

(22) Filed: Sep. 6, 2007

(65) Prior Publication Data

US 2008/0064005 A1 Mar. 13, 2008

Related U.S. Application Data

(60) Provisional application No. 60/842,875, filed on Sep. 7, 2006.

(51) Int. Cl.
*A61C 3/00* (2006.01)
(52) U.S. Cl. .......................... 433/75; 433/76
(58) Field of Classification Search ............... 433/72, 433/74, 75, 76, 213; 24/303
See application file for complete search history.

(56) References Cited

U.S. PATENT DOCUMENTS

| 2,434,320 | A | | 1/1948 | Karlstrom |
| 3,011,259 | A | | 12/1961 | Baum |
| 3,407,503 | A | | 10/1968 | Nealon |
| 3,413,724 | A | | 12/1968 | Segal |
| 3,600,810 | A | | 8/1971 | Marshall et al. |
| 4,060,899 | A | | 12/1977 | Sauter |
| 5,007,836 | A | | 4/1991 | Gayso |
| 5,015,183 | A | | 5/1991 | Fenick |
| 5,133,660 | A | | 7/1992 | Fenick |
| 5,320,529 | A | * | 6/1994 | Pompa ........................ 433/76 |
| 5,556,278 | A | | 9/1996 | Meitner |
| 5,833,693 | A | * | 11/1998 | Abrahami .................... 606/96 |
| 5,842,859 | A | * | 12/1998 | Palacci ........................ 433/72 |
| 5,967,777 | A | * | 10/1999 | Klein et al. ................... 433/75 |
| 6,672,869 | B2 | * | 1/2004 | Rabenstein et al. .......... 433/74 |
| 7,121,827 | B2 | * | 10/2006 | Lampert ...................... 433/72 |
| 7,322,821 | B1 | * | 1/2008 | Lin et al. ...................... 433/72 |

FOREIGN PATENT DOCUMENTS

WO    WO 00/1994026200 A1    11/1994

* cited by examiner

*Primary Examiner*—Cris L Rodriguez
*Assistant Examiner*—Eric Rosen
(74) *Attorney, Agent, or Firm*—Harter Secrest & Emery LLP; Stephen B. Saiai, Esq.; Jodi A. Reynolds, Esq.

(57) ABSTRACT

An apparatus used in forming a template for locating a dental implant osteotomy in a patient's mandible or maxilla. The apparatus includes a guide post and a sleeve having a longitudinal gap. A dental cast of a patient's mandible or maxilla is formed and a hole is drilled in the dental cast wherein the location and orientation of the hole corresponds to a desired location and orientation of the dental implant osteotomy. The guide post is inserted into the hole and the sleeve is magnetically attached. A molding material is applied to a portion of the dental cast and to a portion of an outer surface of the sleeve to form the template. The template, including the sleeve embedded therein, is removed from the dental cast and is used in the patient's mouth to provide a guide means for drilling the osteotomy.

14 Claims, 6 Drawing Sheets

METHOD FOR MAKING AND USING A TEMPLATE FOR LOCATING A DENTAL IMPLANT AND COMPONENTS RELATING THERETO

CROSS-REFERENCE TO RELATED APPLICATIONS

This application claims the benefit of U.S. Provisional Application No. 60/842,875, filed Sep. 7, 2006.

STATEMENT REGARDING FEDERALLY SPONSORED RESEARCH OR DEVELOPMENT

None.

REFERENCE TO A "SEQUENCE LISTING"

None.

TECHNICAL FIELD

The present invention relates to a method for locating a dental implant hole (osteotomy) in a patient's jawbone by construction and use of a template, and to the template and sleeve components thereof.

BACKGROUND OF THE INVENTION

One aspect of contemporary dental surgery involves the use of prosthetic teeth to replace missing teeth. Typically one or more prosthetic teeth are mounted on dental implants which are secured in the jawbone of the recipient. The dental implants must be securely mounted in sufficient bone tissue so that they are as stable as natural teeth roots.

The conventional procedure for installing a dental implant includes drilling a hole in the maxillary or mandibular jawbone of the recipient, inserting the implant in the hole, and attaching a prosthetic tooth to the implant. Various types of dental implants are useful; for example, blades, screws, and cylinders. The dental implant is generally made of titanium or high titanium alloy and the top of the dental implant, which is typically located at the gingiva, is provided with a mating means (usually a top portion and inner threads) for attaching the prosthetic tooth thereto.

The osteotomy must be located the correct distance from adjacent teeth in order to guarantee a proper fit and cosmetic result for the prosthetic device. Furthermore, it is extremely important to accurately locate the osteotomy in the jawbone so that the implant is sufficiently anchored in the bone structure.

Because of the limited space, working within a patient's mouth poses many impediments to easily and precisely locating and making the osteotomy for the implant, and ultimately positioning the prosthetic.

It is known in dental surgery to make a cast impression of the patient's mandible and/or maxilla in order to design or select the appropriate prosthetic device. Moreover, it is known to use the diagnostic tooth set-up or wax-up on a cast to determine the most desirable tooth position in the final restoration. In locating and creating the hole for a dental implant, however, the most commonly used method is simply to survey the area visually and drill according to the visual inspection. In some cases, where the patient is completely or significantly toothless, an acrylic tooth set-up may be used in the patient's mouth to locate the most desirable tooth position in the final restoration. With acrylic tooth set-ups, the surgeon drills through the tooth set-up in order to make a mark on the patient's jawbone. The acrylic set-up is then removed, and the mark is used as the start of the hole for the implant. In other words, the surgeon continues drilling the started hole at a visually determined angle.

Other techniques for locating dental implants are available. For example, U.S. Pat. No. 5,015,183 to Fenick describes a method involving the use of a casting having a radiopaque marker which is inserted into the patient's mouth. A series of x-rays is taken to establish a trajectory for the proposed osteotomy in the patient's jawbone. While the method provides an accurate means to locate the implant hole, it requires multiple x-rays subjecting the patients to undesirable exposure levels, and is expensive.

U.S. Pat. No. 5,556,278 to Meitner describes a method for locating a dental implant hole in a patient's jawbone by constructing a template and using a guide post and a sleeve. However, because of the length or height of the sleeve, it is difficult to Insert the drill bit th rough the top of the sleeve bore and to maneuver the drill bit as a significant amount of space within a patient's mouth is required.

What is needed then is a method and apparatus for accurately, safely, and conveniently locating an osteotomy for a dental implant in the mouth of the implant recipient.

SUMMARY OF THE INVENTION

It is therefore an object of the invention to provide a method for accurately locating one or more dental implant osteotomies in the recipient's jawbone.

It is another object of the invention to provide a method for locating an implant osteotomy in the jawbone which allows a drill to be inserted and removed laterally to reduce the amount of space required to maneuver the drill in a patient's mouth to perform the osteotomy.

It is a further object of the invention to provide a method for locating an implant osteotomy in the jawbone that allows the drill to be irrigated during the drilling of the osteotomy.

It is still a further object of the invention to provide a method for locating an implant osteotomy in a jawbone that allows the use of an inexpensive drill bit in a straight dental handpiece for making a pre-osteotomy implant guide hole in a cast arch.

In accordance with the forgoing objects, the present invention includes a method for making a template for a dental implant osteotomy in an edentulous space of a patient's mandible or maxilla for locating an appropriate number of diagnostic tooth setups, involving the steps of making a dental cast of the patient's mandible or maxilla including the edentulous space; drilling a hole into the dental cast wherein the location and orientation of the hole correspond to a desired location and orientation of the dental implant osteotomy; inserting a guide post into the hole; attaching a sleeve to the guide post, the sleeve having a top surface, a bottom surface, an inner annular surface generally corresponding to a curved outside surface of the guide post and a longitudinal gap extending through the top surface towards the bottom surface; applying a template-forming molding material to a portion of the dental cast and to a portion of an outer surface of the sleeve, allowing the molding material to cure; and, removing the cured template including the sleeve embedded therein from the dental cast, whereby using the template in the patient's mouth provides a guide means for drilling the osteotomy.

A person skilled in the art will be able to determine the size of the portion of the dental cast that it is necessary to apply the template-forming molding material, that is, whether the impression need include the lingual surface and/or the occlusal surface of one or more teeth, or the entire maxilla or mandible of the recipient, and the size or extent of the template for ultimate use in the patient's mouth.

The invention also includes the step of radiographically visualizing the correct location and orientation of the radiopaque sleeve in the patient's mouth in an oblique, horizontal or axial plane via a panorex radiograph, computer assisted tomography (CAT scan), linear tomography, periapical x-ray, or other internal visualization technique, and using the resulting visualization in conjunction with the dental cast impression to evaluate, and if necessary change, the position of the sleeve in a horizontal and/or an oblique plane prior to preparing the osteotomy site.

The invention further includes the step of applying a layer of lubricating material, such as wax or other suitable material, over a portion of the dental cast, including the edentulous space and adjacent regions where a template-forming material will be applied, prior to applying the molding materials to the dental cast to facilitate removal of the template from the cast impression once the template is cured.

The method thus described is not limited to the location of a single implant osteotomy, but the technique applies equally to locating more than one implant osteotomy in one or more edentulous spaces in a patient's mouth.

The template used for locating the osteotomy in a patient's mandible or maxilla according to the invention includes a cured, resinous base. The underside contour of the template corresponds to the implant recipient's jaw bone including the edentulous space. The material of the template is a self-curing or light-curing resin or other material suitable for the construction of dental templates. The template also includes at least one sleeve having a longitudinal gap extending through the top surface towards the bottom surface. The sleeve also has a boss projecting transversely from a portion of an outer surface of the sleeve, which improves the strength of the resin-to-sleeve bond. The sleeve is at least partially embedded in the template such that when the template is inserted into the patient's mouth, the sleeve provides a precise guide for the drill bit used by the surgeon in drilling the osteotomy in the patient's jaw bone.

In one aspect of the invention, the sleeve comprises an inner annular surface, a top surface, a bottom surface and a longitudinal gap extending through the top surface towards the bottom surface. The sleeve fits around a guide post and ultimately, the longitudinal gap is large enough to receive a drill bit wherein the sleeve minimizes lateral movement of the drill bit. That is, the longitudinal gap of the sleeve is preferably of a width that is less than or equal to the diameter of the sleeve; i.e, a substantially half-cylindrically shaped, c-shaped or u-shaped sleeve. Either the sleeve or guide post contains a magnet, or is magnetized, to attract the other. In an aspect of this embodiment, at least one boss projects transversely from a rear portion of the sleeve to provide additional surface area for securing the sleeve in the template-forming resin.

All of the sleeve embodiments are preferably constructed of ferromagnetic materials, stainless steel, titanium, or non x-ray scattering ceramic.

The present invention also includes a method for making a template for locating dental implant osteotomy in a patient's mandible or maxilla involving the steps of drilling an opening in a guide post; inserting a magnet into the opening; sealing the opening to form a magnetic guide post; drilling a hole into a dental cast of the patient's mandible or maxilla, wherein the location and orientation of the hole correspond to a desired location and orientation of the dental implant osteotomy; inserting the guide post into the hole; magnetically attaching a sleeve and the magnetic guide post, the sleeve having a top surface, a bottom surface and a longitudinal gap extending through the top surface towards the bottom surface, large enough to receive a drill bit laterally, for making the osteotomy; and, applying a template-forming, molding material to a portion of the dental cast and to a portion of an outer surface of the sleeve and portions of the dental cast. In another aspect of the invention, the sleeve contains or is made from magnetic material.

The invention will now be described in detail in terms of the drawings and the description which follow.

BRIEF DESCRIPTION OF THE DRAWING FIGURES

DETAILED DESCRIPTION OF THE INVENTION

At the outset, it should be appreciated that the use of the same reference number throughout the several figures designates a like or similar element.

Figure 1:
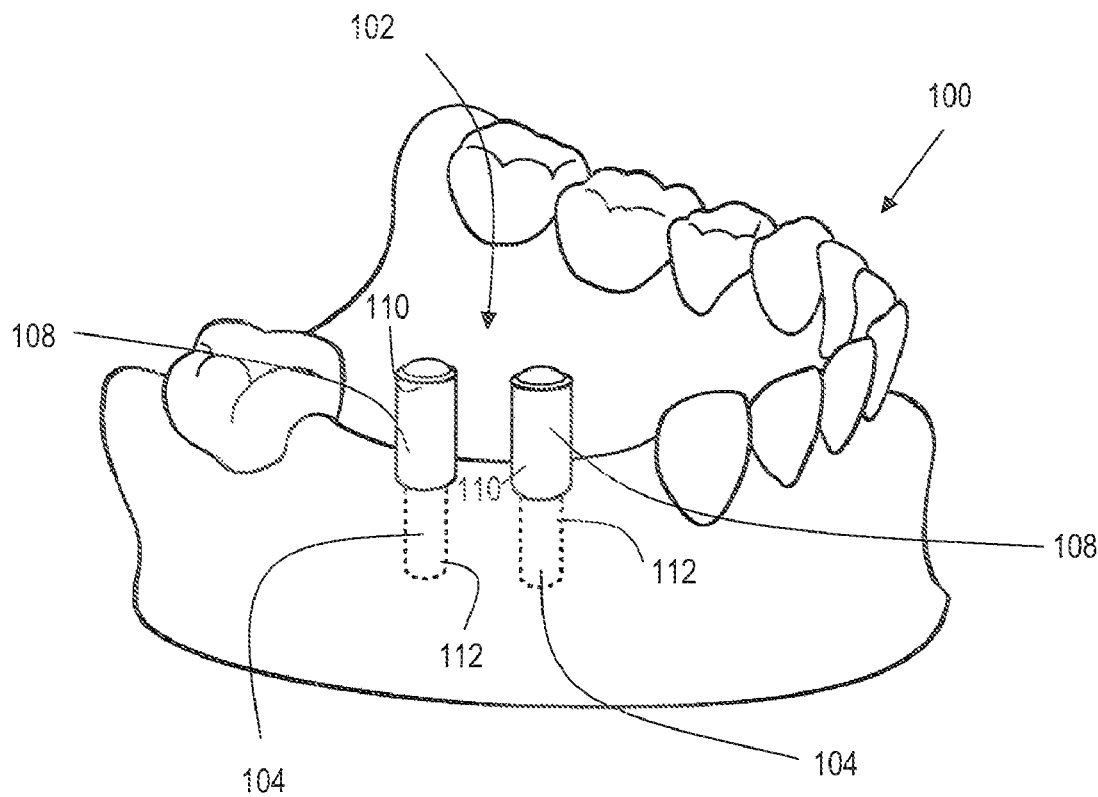
FIG. 1 is a perspective view of a dental cast impression of a portion of a human mandibular jawbone showing a number of teeth and an edentulous space having two guide post inserted therein.

Referring now to the figures, FIG. 1 is a perspective view of a dental cast impression 100 of a patient's mandible or maxilla jaw bone having an edentulous space 102 where at least one tooth has been lost and is to be replaced by a dental implant. A method for making a template for a dental implant osteotomy in the edentulous space 102 of a patient's mandible or maxilla comprises forming the dental cast impression 100. The dental cast impression 100 includes the edentulous space 102, and adjacent regions including the lingual surface of a tooth adjacent one side of the edentulous space where the implant will be located and/or an occlusal surface of a tooth adjacent one side of the edentulous space where the implant will be located, and is typically made in alginate and poured up, preferably, in cast stone. Cast stone is preferred over die stone because the relatively softer cast stone permits the use of a drill bit for making the implant guide hole in the cast arch, as will be more fully described below.

Figure 4:
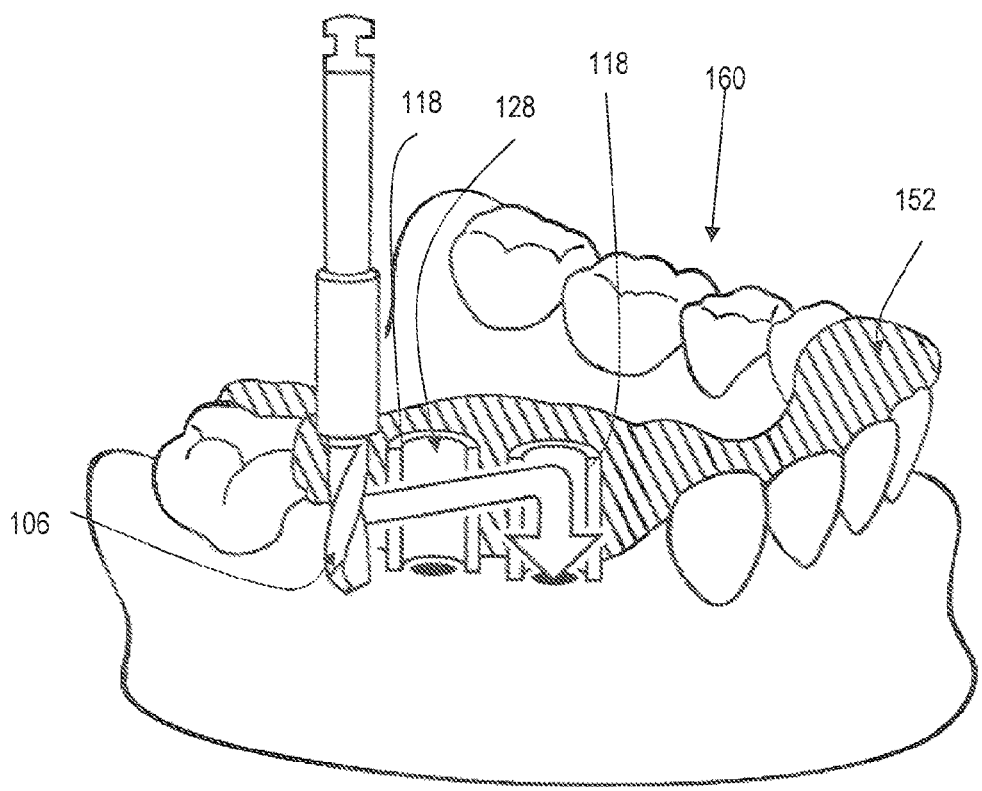
FIG. 4 is a perspective view of the resin template arranged in a patient's mouth showing the sleeve embedded in the template and the direction for inserting a drill bit through the sleeve.

A hole 104 is drilled into the cast 100 with a drill bit 106 (shown in FIG. 4). The hole 104 is drilled at a desired location and orientation based on the optimum location and orientation of the prosthetic implant in the patient's mandible or maxilla jaw bone. Such optimum location and orientation of the prosthetic implant is based, in part, on the height and orientation of the adjacent and opposing teeth, the spacing between the edentulous space 102, and the height and width of the patient's bone. Preferably, the hole 104 is made with a standard, inexpensive $3/32$'s inch diameter drill bit which conveniently fits in a dental laboratory handpiece. The depth of the hole 104 is preferably at least 10 mm.

Figure 7:
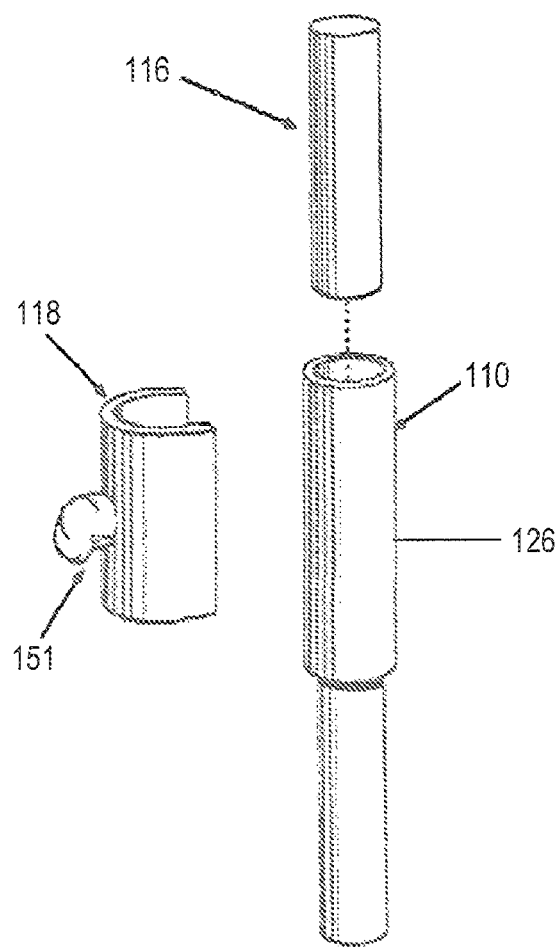
FIG. 7 is a perspective view of the guide post receiving a magnet, and the sleeve.
Figure 8:
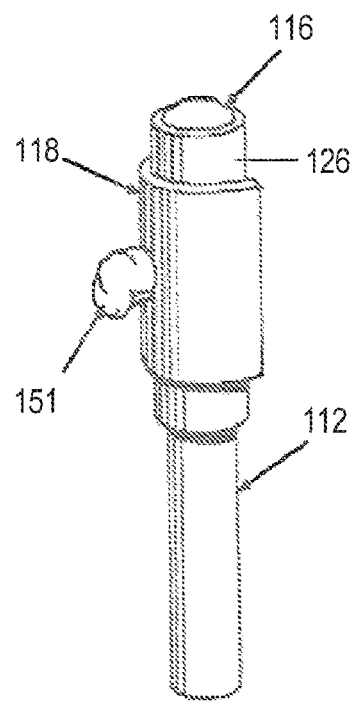
FIG. 8 is a perspective view of the sleeve attached to the guide post.
Figure 9:
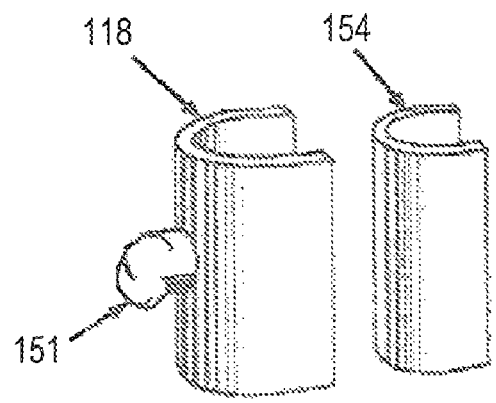
FIG. 9 is a perspective view of a sleeve insert to be disposed in the sleeve for reducing the sleeve size.
Figure 10:
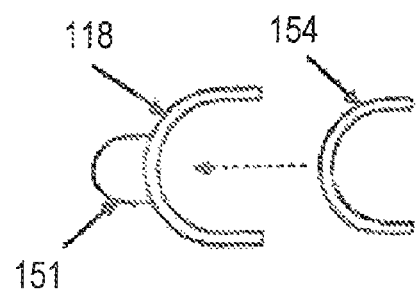
FIG. 10 is a top view of the sleeve insert to be disposed in the sleeve for reducing the sleeve size.
Figure 11:
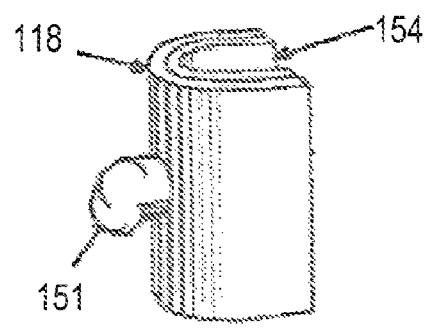
FIG. 11 is a perspective view of the sleeve insert disposed within the sleeve for reducing the sleeve size.
Figure 12:
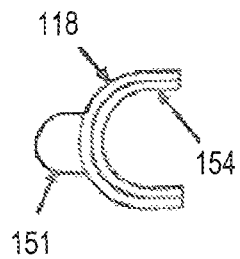
FIG. 12 is a top view of the sleeve insert disposed within the sleeve for reducing the sleeve size.
Figures 13, 14:
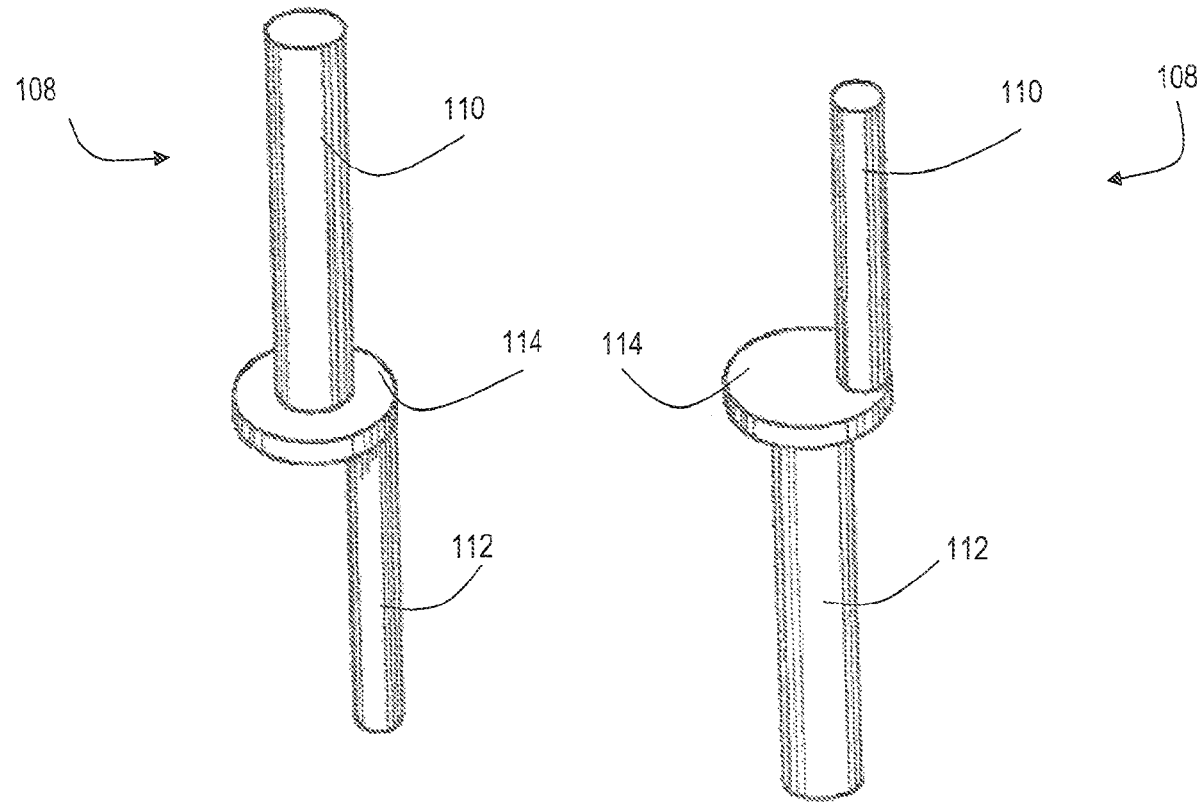
FIG. 13 is a perspective view of another embodiment of the guide post having an upper shaft centrally positioned on a base and a lower shaft off-center from the base.
FIG. 14 is a perspective view of another embodiment of the guide post having the upper shaft disposed off-center from the base and the lower shaft centrally positioned on the base.

After the hole 104 is drilled, a guide post 108 is inserted into the hole 104. The guide post 108 preferably includes an upper shaft 110 and a lower shaft 112, wherein the lower shaft 112 has a diameter corresponding to the diameter of the hole 104. That is, the lower shaft 112 preferably has a $3/32$'s inch diameter. As shown in FIGS. 13 and 14, the guide post 108 may further comprise a base 114 wherein the upper shaft 110 is centrally positioned on the base 114 and the lower shaft 112 is off-set from the center of the base 114. Alternatively, the guide post 108 can be constructed such that the upper shaft 110 is off-set from the center of the base 114 and the lower shaft 112 is centrally positioned on the base 114. In either configuration, the upper shaft 110 and/or lower shaft 112 can be disposed along the base 114 at an angle. Such off-set configurations allow the guide post 108 and ultimately, the prosthetic implant to be adjustably positioned along a longitudinal axis that differs from the longitudinal axis of the lower shaft 112. Thus, multiple locations and orientations of the prosthetic implant can be achieved. In one embodiment, the upper shaft 110 includes an opening for receiving a magnet 116. Preferably, the opening is a centrally positioned aperture for receiving the magnet 116 as shown in FIGS. 7 and 8. The magnet 116 is affixed in the opening with epoxy, or other suitable material.

Figure 2:
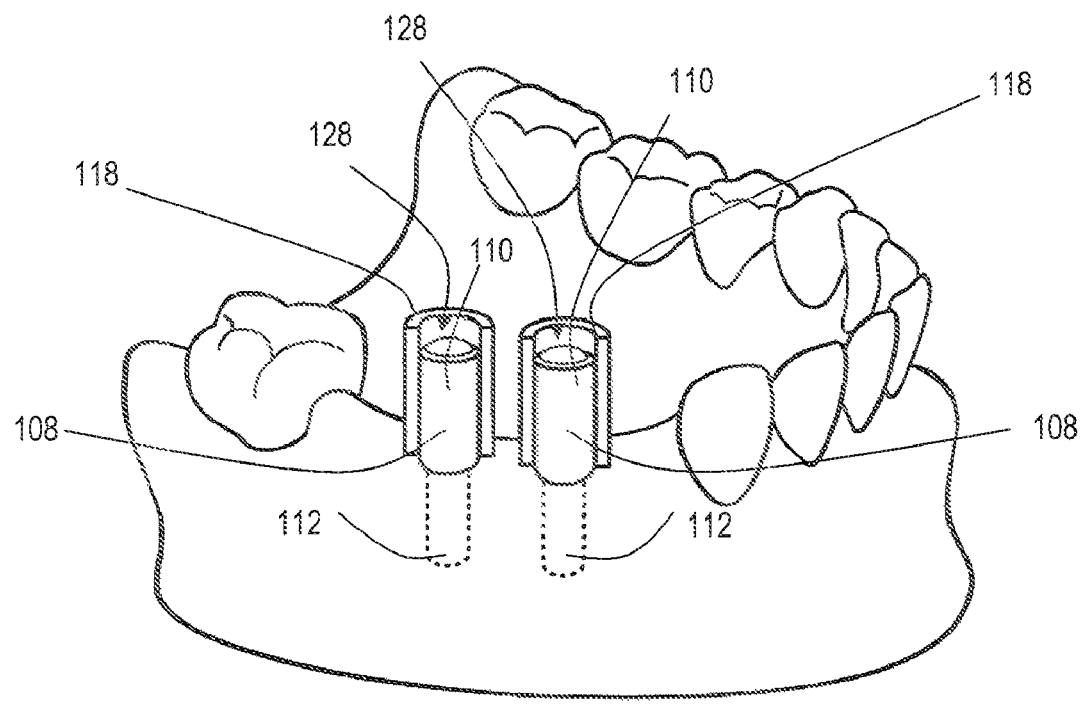
FIG. 2 is a view similar to FIG. 1 but showing two sleeves attached to the guide post, each having a longitudinal gap for receiving a drill bit.
Figure 3:
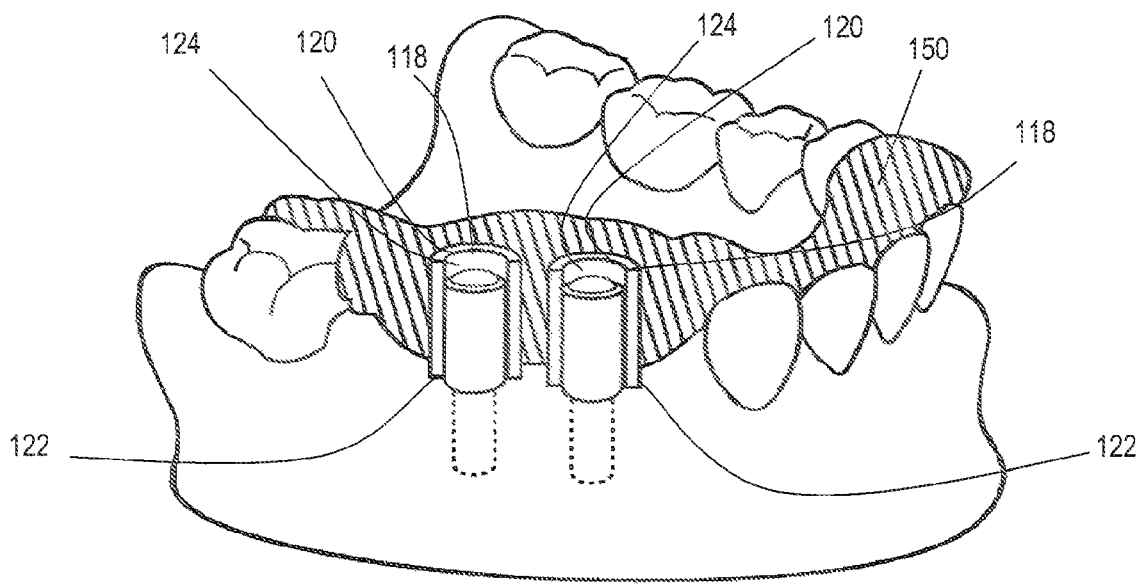
FIG. 3 shows a resin template molding material applied to the dental cast in and around the sleeves and the lingual and occlusal surfaces of some of the adjacent teeth.

Referring now to FIGS. 2 and 3, a sleeve 118 is magnetically attached to the guide post 108. The sleeve 118 includes a top surface 120, a bottom surface 122, and an inner annular surface 124. The inner annular surface 124 generally corresponds to a curved outside surface 126 of the guide post 108, as shown in FIG. 8, and a longitudinal gap 128 extends through the top surface 120 towards the bottom surface 122. That is, the longitudinal gap 128 may extend through the bottom surface 122 or alternatively may extend only partially along the side of the sleeve 118. The sleeve 118 is attached laterally to the guide post 108 until the bottom surface 122 of the sleeve 118 contacts the dental cast 100. Alternatively, the sleeve 118 is slid over the guide post 108 until the bottom surface 122 of the sleeve 118 contacts the dental cast 100. Preferably, the longitudinal gap 128 has a width that is slightly less than or equal to a diameter of the sleeve 118, such that the sleeve 118 is substantially half-cylindrically. The longitudinal gap 128 width, however, can vary such that the sleeve 118 is substantially c-shaped or u-shaped. It should be appreciated that the diameter of the bore of the sleeve 118 will be large enough to allow the sleeve 118 to be attached to the guide post 108. The sleeve 118 is preferably made from a material that is attracted to the magnetic guide post 108, such as ferrous metals or other suitable types of material. The sleeve may also be constructed from stainless steel or titanium. It is also possible to have the sleeve constructed from non x-ray scattering ceramic. It should be understood that the sleeve may contain a magnet and the guide post can be constructed from a material that is attracted to the magnetic sleeve magnet. For example, the sleeve may be constructed of a ceramic magnet and the guide sleeve constructed from a metal alloy attracted to the ceramic magnet.

As shown in FIG. 3, a moldable, template-forming material 150 is applied to the dental cast 100 around the sleeve(s) 118 in the edentulous space 102 and around at least one tooth adjacent to the edentulous space 102. The extent of the template material 150 around adjacent teeth will be determined by the amount of stability required of the template 150 and can be determined by one having ordinary skill in the art when the template 150 is being constructed. The template material 150 will preferably be a self curing, temperature sensitive reversible thermoplastic or light curing resin, although any suitable material can be used. One or more bosses or brackets 151, shown in FIGS. 7 and 8, project transversely from a portion of an outer surface of the sleeve 118 to help anchor the sleeve 118 in the resinous material. The boss 151 can be fixedly secured to the outer surface of the sleeve 118 by welding, adhering or by fixedly securing the boss 151 by other suitable means. Prior to applying the template-forming material, any undercuts can be blocked with wax or other suitable material and a layer of lubricating material, such as wax or other non-bonding, separating medium, may be applied over a portion of the dental cast, including the edentulous space 102 and the adjacent regions where the template-forming material 150 will be applied.

The template-forming material is allowed to cure. A cured template 152 has formed which includes the sleeve(s) 118 embedded therein. When the template is removed from the dental cast 100, the guide post(s) 108 will either remain in the dental cast 100 or is otherwise separated from the sleeve 118. As shown in FIG. 4, once the template 152 is removed from the dental cast 100, it can be inserted into the patient's mouth 160 by aligning the underside contour of the template 152 with the recipient's adjacent teeth. The template 152 shows two sleeves 118 included in the template 152, however, it should be understood that the template 152 can be created for one or multiple implants, including a plurality of sleeves 118 in the template 152.

The template 152 is correctly located and positioned in the patient's mouth 160 by radiographically visualizing the template's 152 position before the osteotomy is drilled. This can be accomplished by taking one of a panorex, liner tomography, or periapical x-ray or CAT scan. The information obtained from such an evaluation can be used to confirm or alter the parameters of the sleeve 118 to provide the optimum drilling position for the osteotomy.

Figure 5:
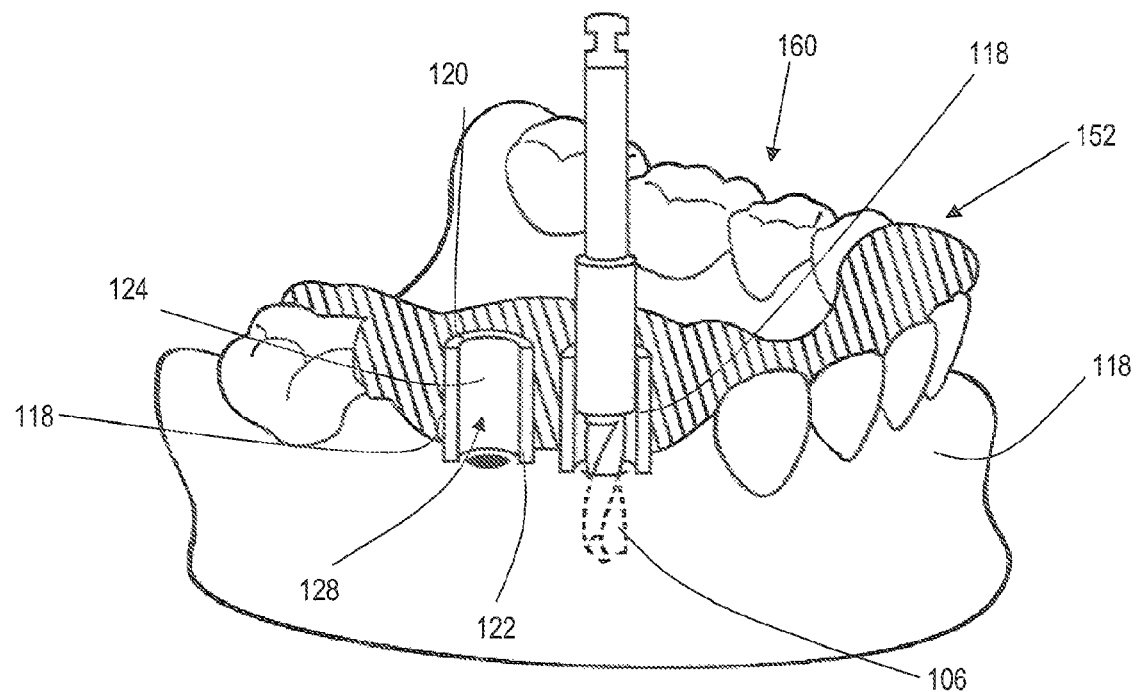
FIG. 5 is a view similar to FIG. 4 but showing the drill bit being inserted into the sleeve through the patient's mandible.

As shown in FIGS. 4 and 5, the longitudinal gap 128 of the sleeve 118 provides an opening for, and is large enough to receive, a surgical drill bit 106 for making an osteotomy. It should be appreciated by one having ordinary skill in the art that the sleeve size and the angle of the opening can be reduced by inserting a sleeve insert 154, as shown in FIGS. 9-12, wherein the inner annular surface of the sleeve 118 corresponds with the outer annular surface of the sleeve insert 154. Inserting the drill bit 106 laterally through the longitudinal gap, rather than from the top, permits operations in small spaces including in the posterior regions of a patient's mouth 160. Further, the longitudinal gap 128 allows one to view the drilling of the osteotomy and provides access to the region for irrigation purposes to cool the surgical drill while the osteotomy is being made.

Figure 6:
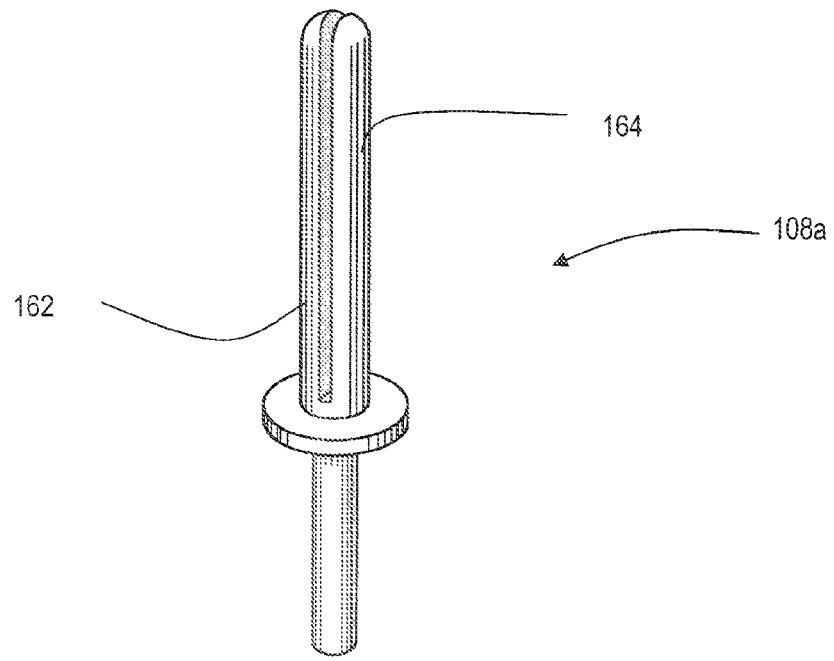
FIG. 6 is a perspective view of another embodiment of the guide post having a slit-center for frictionally engaging the sleeve.

Another embodiment of the guide post 108a is shown in FIG. 6. The guide post 108a includes a longitudinally slit-center forming two spring-bias prongs 162, 164 for frictionally engaging the sleeve 118. Thus, rather than magnetically attaching the sleeve 118 to the guide post 108, the sleeve 118 can be held into place by the guide post 108a frictionally engaging the sleeve 118. It should be understood that other configurations of guide posts are possible.

There has thus been described a method for locating a dental implant osteotomy in a patient's jawbone; a method for forming a template used for optimizing the location and position of the osteotomy; and apparatus used in conjunction with the above described methods. Those skilled in the art will recognize that modifications may be made in the method and apparatus described herein without departing from the true spirit and scope of the invention which accordingly are intended to be limited solely by the appended claims.

The invention claimed is:

1. An apparatus used in forming a template for locating a dental implant osteotomy in a patient's mandible or maxilla, comprising:
    a guide post having a curved outer surface, a predetermined diameter, a magnet and a centrally positioned aperture, wherein the magnet is disposed and sealed within the centrally positioned aperture; and
    a sleeve having a sidewall that includes a top surface, a bottom surface, an outer annular surface, and an inner annular surface generally corresponding to the curved outer surface of the guide post, the sleeve having a longitudinal gap extending all the way through the sidewall from the inner annual surface to the outer annular surface and all the way through the sidewall from the to surface to the bottom surface, and a diameter greater than the diameter of the guide post, wherein the guide post magnetically engages a portion of the inner annual surface of the sleeve so that the sleeve is attached to the guide post.

2. The apparatus of claim 1 further comprising an insert corresponding to the inner annular surface of the sleeve and having a longitudinal gap extending through the top surface towards the bottom surface and aligning with the longitudinal gap of the sleeve, wherein the insert is configured to reduce the diameter of the sleeve.

3. The apparatus of claim 1 in which the guide post includes an upper shaft, a lower shaft and a base, wherein the upper shaft is centrally positioned on the base, and the lower shaft is off-set from the center of the base.

4. The apparatus of claim 1 in which the guide post includes an upper shaft, a lower shaft and a base, wherein the lower shaft is centrally positioned on the base and the upper shaft is off-set from the center of the base.

5. The apparatus of claim 1 wherein the sleeve includes a boss projecting transversely from a portion of an outer surface of the sleeve.

6. The apparatus of claim 1 in which the longitudinal gap of the sleeve has a width that is less than or equal to a diameter of the sleeve.

7. The apparatus of claim 1 in which the longitudinal gap of the sleeve is large enough to laterally receive a drill for making the osteotomy.

8. The apparatus of claim 1 further including a cured, resinous base having an impression of the patient's mandible or maxilla including the edentulous space, wherein the sleeve is at least partially embedded in the resinous base and fixed in the template in a position and at an angle corresponding to the desired position and angle of the osteotomy.

9. The apparatus of claim 1 in which the sleeve is substantially half-cylindrically shaped.

10. The apparatus of claim 1 in which the sleeve is substantially-c-shaped.

11. The apparatus of claim 1 in which the sleeve is substantially u-shaped.

12. The apparatus of claim 1 in which the sleeve is constructed from one of stainless steel and titanium.

13. The apparatus of claim 1 in which the sleeve is constructed from ferromagnetic material.

14. The apparatus of claim 1 in which the sleeve is ceramic.

* * * * *